United States Patent [19]
Krämer

[11] Patent Number: 4,581,009
[45] Date of Patent: Apr. 8, 1986

[54] CENTRIFUGE, PARTICULARLY SOLID BOWL CENTRIFUGE FOR SOLIDS/LIQUID SEPARATION OF SLUDGES

[75] Inventor: Paul Krämer, Cologne, Fed. Rep. of Germany

[73] Assignee: Klöckner-Humboldt-Deutz AG, Fed. Rep. of Germany

[21] Appl. No.: 640,799

[22] Filed: Aug. 14, 1984

[30] Foreign Application Priority Data

Aug. 17, 1983 [DE] Fed. Rep. of Germany ....... 3329669

[51] Int. Cl.⁴ ............................................... B04B 9/00
[52] U.S. Cl. ...................................... 494/37; 494/32; 494/53; 494/84
[58] Field of Search ..................... 210/170, 603, 609; 494/31, 32, 37, 42, 49, 50, 51, 52, 53, 54, 55, 84, 85, 900

[56] References Cited

U.S. PATENT DOCUMENTS 2,541,630  2/1951  Yeomans ............................ 210/603
3,813,030  5/1974  Curtin ................................. 494/32
4,073,431  2/1978  Jager .................................. 494/84
4,076,515  2/1978  Rickard ............................. 210/603
4,228,949  10/1980 Jackson ............................. 494/84
4,327,862  5/1982  Jakobs ............................... 494/84
4,354,936  10/1982 Ishida ............................... 210/603

Primary Examiner—Robert W. Jenkins
Attorney, Agent, or Firm—Hill, Van Santen, Steadman & Simpson

[57] ABSTRACT

A mechanism and method for treating sludge material for separating the material into solid and liquid phases in a centrifugal separator having a rotating drum and an advancing screw driven at a speed differential relative to the drum, conveying a solid phase of the sludge to a digester tower for generating a biogas, delivering the biogas to a collection chamber and feeding the biogas to a gas powered prime mover connected to drive the centrifugal separator through a hydraulic pump and motor drive with the biogas generated and supplied to the motor commensurate with the speed of operation of the separator.

9 Claims, 2 Drawing Figures

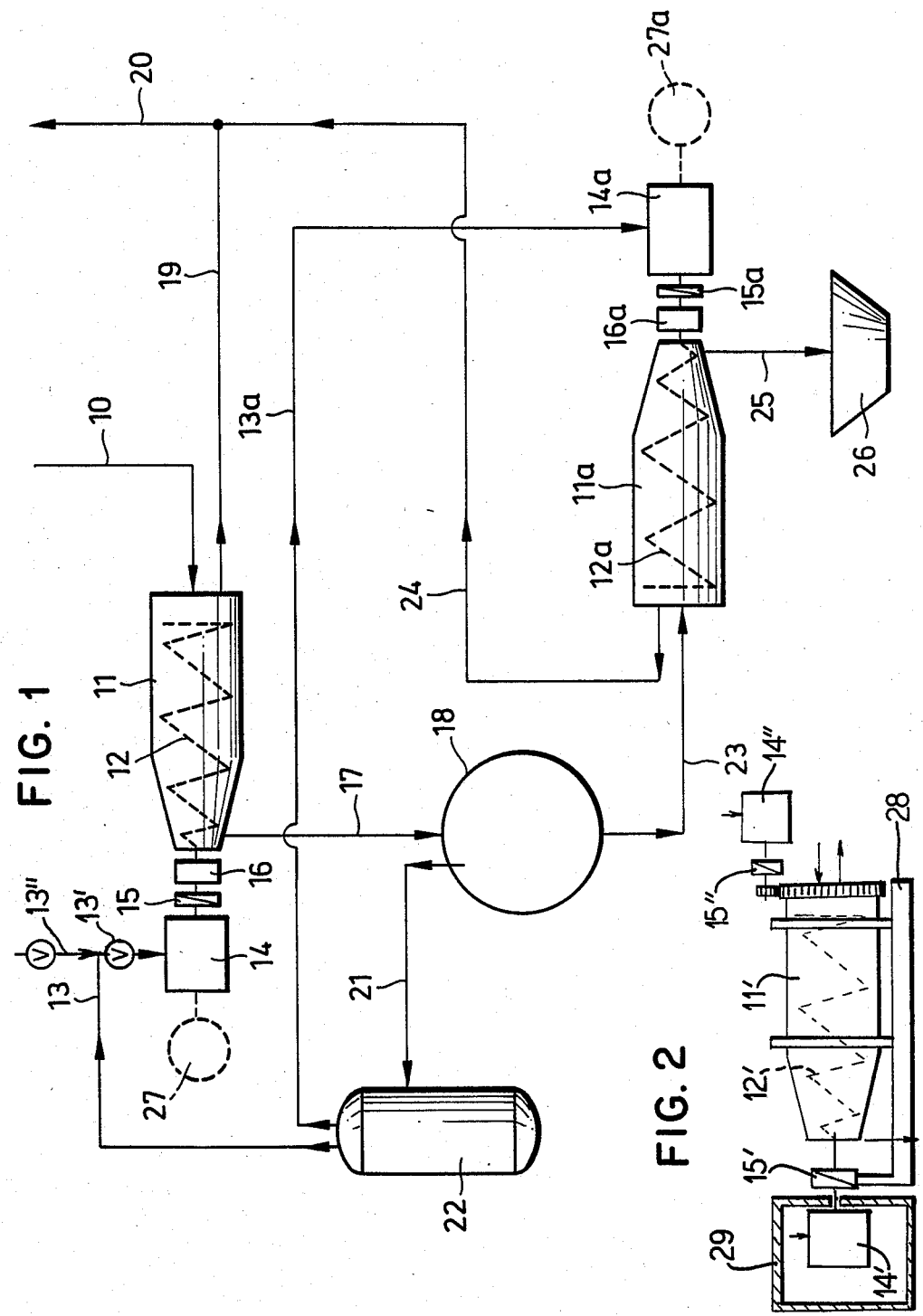

CENTRIFUGE, PARTICULARLY SOLID BOWL CENTRIFUGE FOR SOLIDS/LIQUID SEPARATION OF SLUDGES

BACKGROUND OF THE INVENTION

The present invention relates to improvements in centrifuge separating systems, and more particularly to an improved solid drum and worm centrifuge for the separation of sludges into a solid phase and a liquid phase, and particularly sludges from the biological clarification stage of a sewage treatment plant where the sludge has a capability of generating a biogas, and a prime mover system for driving the centrifuge.

Centrifuge separating systems are employed universally for sludge dewatering or sludge thickening of sludges. An example of this type of operation is in the treatment of municipal sludges in sewage treatment plants. Solid drum or bowl centrifuges which have an advancing screw or worm therein are utilized to dewater or separate thin sludges low in solids as well as thick slurries high in solids and these systems are used widely in sewage treatment plants. With a solid bowl worm centrifuge of the type described, the solids particles are settled or separated onto the inner surface of the centrifuge drum by the action of centrifugal force and these are moved of discharged by the conveyor screw which rotates independently inside the rotating drum with a differential speed which is either slower or faster, that is, it leads or lags in comparison to the rotational speed of the drum.

It has heretofore been the practice in driving the centrifuge of a solid bowl worm separator used in sewage treatment plants by an electric motor. Normally, this is a three phase AC motor or a DC motor.

It is also known in the driving of a solid bowl worm centrifuge that the electric motor drives the centrifuge through a hydraulic drive mechanism which incorporates a hydraulic pump delivering its liquid to a hydraulic motor which is in driving connection with the separator. Normally, the drive will be connected to both the conveyor screw and the drum with a gearing arrangement such as a planetary gear or a controllable speed differential gearing arrangement interconnecting the drum and screw to obtain the desired speed differential.

In the separation process utilizing sewage sludge, gas is generated and this gas is eliminated by burning. The gas essentially consists of methane and is conveniently referred to as biogas which develops in the digestion tower of a sewage treatment plant as a result of digestion or fermentation of the sludge resulting from the biological clarification stage. Motors operative on this biogas have been used to drive generators and the electrical output of the generators has been used to power electrical motors which have been used to drive the centrifuges and the supply of electrical current has resulted partially from the biogas generators as well as outside sources. Such a drive system for a centrifuge requires high capital costs as well as high operating costs because the overall efficiency of the drive system cannot be high due to the number of energy conversions necessary from the beginning of the chain to the driving of the centrifuge. On the other hand, systems wherein biogas is produced from the biomass on the basis of microbiological and biochemical processes and wherein thin sludges or thick slurries must be dewatered or thickened are increasing in number.

It is, therefore, an object of the present invention to provide a centrifuge system utilizing a solid bowl worm centrifuge for the separation of solids or liquids from sludges which will be more effective and more efficient than heretofore available.

In accordance with the principles of the invention, a system is utilized wherein the drive of the centrifuge is provided by an essentially direct gas motor drive operated from biogas as a fuel.

Various advantages are achieved by the invention including the fact that wherein the centrifuge is driven directly by a biogas operated motor utilizing a hydraulic pump and a hydraulic motor, these elements normally already exist in systems provided and the electric drive motor and current generator for the electric motor are eliminated, this effecting a considerable savings of capital cost. The specific energy consumption or, in other words, the operating cost of the present system are considerably lower due to the reduction of energy conversion stages in the drive system and due also to the increase in overall efficiency connected with a better energy exploitation of the biogas which results from the anaerobic sludge treatment of a sewage treatment plant. Due to the direct employment of the biogas arising in a sewage treatment plant or similar system which generates biogas for the direct drive of the sludge centrifuge, energy self-sufficiency of the system is realized or at least noticeably increased. The more efficient exploitation of the energy contained in the biogas such as in sewage treatment plants becomes more important in view of the fact that systems for the treatment of sewage are becoming more sophisticated out of necessity due to the tightening of environmental protection laws and an increasing quantity of sewage sludge and thus of biogas resulting therefrom. In the event of a shortage of biogas, the gas motor serving as the drive for the centrifuge can be operated with alternative fuel such as natural gas, propane and the like. The waste heat of the biogas motor which is removed by means of its coolant and exhaust gases can likewise be utilized.

It is another feature of the present invention to provide a solid bowl worm centrifuge which can be driven by a single biogas operated motor via a hydraulic drive which comprises a hydraulic pump and two hydraulic motors which can be separately driven via respective dual biogas motors. Self-employment of biogas arising in the sewage treatment plant for the drive of the sludge centrifuge provides a further feature in that the biogas motor is connected by a gasline to a biogas tank which connects the biogas of a digestive sludge tower of the clarification plant where the sludge is being thickened or dewatered. The biogas motor can advantageously be disposed separated from the centrifuge such as in a sound insulated room. The base frame of the centrifuge then will no longer carry the drive motor and the weight of the centrifuge and its vibrations are thereby reduced. According to a further feature of the invention, the centrifuge with the hydraulic pump and motor, but without the biogas motor can be mounted on an undercarriage and thus be movable to various places of employment. The possibility is also provided for the biogas motor to drive a further electric generator in addition to the hydraulic pump of the hydraulic drive. This means that with an excess of biogas which is not needed for driving the centrifuge, this excess can be utilized for supplying additional power such as to consumers in the area of the sewage treatment plants.

Other objects, advantages and features of the invention will become more apparent with the teaching of the principles of the invention in connection with the disclosure of the preferred embodiments thereof in the specification, claims and drawings, in which:

DESCRIPTION OF THE DRAWINGS

FIG. 1 is a schematic illustration of a form of sludge treatment system embodying the principles of the present invention; and FIG. 2 is a fragmentary schematic view illustrating another form of the invention.

DESCRIPTION OF THE PREFERRED EMBODIMENTS

In FIG. 1 a flow chart is illustrated schematically showing the treatment of sludge which is supplied through an inlet line 10 and which may come from the biological clarification stage or aerobic stage of a sewage treatment plant which is not shown in the drawing.

The sludge in the line 10 is first thickened or separated in a solid bowl worm centrifuge which includes a rotatably supported centrifuge drum 11 having a conveyor screw 12 relatively rotatably mounted coaxially therein. While shown schematically, the structure of the centrifuge will be recognized by those versed in the art and the outside contour of the drum and conveyor screw are essentially cylindrical and conically designed toward the solids discharge end. The centrifuge is driven by a biogas motor 14 operated by a biogas supplied through a line 13. The motor 14 drives the centrifuge through drive coupling 15 which connects to the centrifuge through a hydraulic system which includes a hydraulic pump delivering hydraulic fluid to a hydraulic motor for the drive of the centrifuge. The arrangement is connected such that a drive is provided both for the drum and the screw driving them at controllably regulated differential rotational speeds.

The drive of the solid bowl worm centrifuge can also be accomplished by driving from both ends, i.e., that is from separate biogas operated motors as is illustrated in FIG. 2. In FIG. 2 the motor 14' drives through a drive mechanism 15 to connect to a rotary advancing screw 12'. A drum 11' is driven by a separate biogas supplied motor 14" which drives the drum through a drive mechanism 15". In the arrangement of FIG. 2, the drive 15' and the separator 11', 12' are mounted on a common undercarriage or beam structure 28 which permits the units to be disconnected from the drive motor 14' and moved. The motor is shown as enclosed in a sound insulated housing 29 which essentially acoustically separates the motor 14' from the centrifuge.

In either the drive arrangement of FIGS. 1 or 2, the drum 11 or 11' rotates at speeds of, for example, 700 to 1400 rpm usually at a constant rotational speed with the speed chosen to correspond to the type of sludge being processed. The conveyor screw 12, or 12' has a rotational speed which leads or lags with differential speeds of, for example, 1 to 20.

The control of the conveyor worm 12 of the centrifuge is such that the conveyor screw always runs fast enough or slowly enough relative to the drum so that the drum and worm are not plugged by the solids. The control of the speed is accomplished by a controlled flow of hydraulic fluid by a servo or valve control connected to the output of the hydraulic pump of the hydraulic drive 16. It is also contemplated that speed control will be accomplished by control of the biogas flow through the line 13 to the motor 14 such as by a control valve 13'. Normally, there will be a correlation between the amount of biogas produced and the power output required of the motor 14 to drive the separator so that the correlation is automatically accomplished by the production of gas corresponding to the size and speed of operation of the centrifuge. The calorific value of the biogas supplied and burned by the motor is subject to considerable fluctuation as will be understood and for this purpose a secondary supply line 13" with a valve control may be provided supplying additional or make-up commercial gas.

The thickened sludge discharged from the centrifuge 11, 12 flows through conduit 17 into a digestion gas generating tower 18 of the anaerobic stage of the sewage treatment plant. The concentrate of the centrifuge is returned through conduits 19, 20 into the aerobic stage of the sewage treatment plant.

Biogas is generated in the digestion tower 18 as a result of a digestion or fermentation process. The biogas is supplied through a conduit 21 to a biogas collection tank 22. From the collection tank the biogas is supplied through the conduit 13 to the biogas motor 14. The motor 14 is basically a prime mover and usually will be an internal combustion engine capable of operating on a combustible gas such as methane, and in some circumstances a diesel type of engine may be employed.

In the form shown in FIG. 1, the digested sludge leaves the digestion gas generating tower 18 via a conduit 23 into a further or second solid bowl worm centrifuge having a drum 11a and a screw conveyor 12a. This second centrifuge is driven by a second biogas motor 14a also supplied with biogas through a line 13a leading from the gas collection tank 22. The motor 14a is connected through a coupling 15a to a hydraulic drive 16a including a pump and a hydraulic motor drivingly connected to the drum 11a and worm 12a to drive them in rotation at differential speeds. The centrifuged liquid resulting from processing in the second centrifuge is returned via conduits 24 and 20 to the sewage treatment plant. The largely dewatered digested sludge 25 from the second centrifuge is discharged through a line 25 to a utilization point 26 such as storage means of for use in agriculture or for burning.

In accordance with the concepts of the invention, it is contemplated that the biogas motors 14 and 14a will also be connected to drive generators 27 and 27a. In addition to the hydraulic pump of the hydraulic drive 16, 16a of the centrifuge, the generators 27 and 27a generate electric power with which power consumers of the sewage treatment plant are supplied such as for use for electric drive motors or conveyor pumps of the like. The biogas motors 14 and 14a may be constructed having two shafts, one driving the centrifuge and the other driving the generator.

According to a feature of the invention, the biogas motors 14 and 14a are spatially separated from the centrifuge and each may be positioned or situated as shown in FIG. 2 in a sound insulated room. This affords an advantage in that the centrifuge can be relieved of its drive motor which is an advantage relative to weight and vibration.

Thus, it will be seen that there has been provided an improved centrifuge system which can be self-contained, which is self-regulating in that the energy production corresponds to the energy consumption, and which meets the objectives and advantages above set forth.

I claim as my invention:

1. A centrifuge system for treating and separating the solids and liquid phases of sludge of the type which generates biogas comprising in combination:
   a centrifugal separator having a sludge inlet and outlets for the liquid phase and solid phase resulting from separation;
   biogas generating means receiving the solids separated out in said separator and arranged to generate biogas therefrom;
   a drive connected to drive the separator;
   and a biogas operated motor receiving biogas from said biogas generating means and connected to said drive for direct driving of the separator.

2. A centrifuge system for treating and separating the solids and liquid phases of sludge of the type which generates biogas constructed in accordance with claim 1:
   wherein said drive includes a hydraulic pump driven by the motor and a hydraulic motor drivingly connected to the separator and driven by the pump.

3. A centrifuge system for treating and separating the solids and liquid phases of sludge of the type which generates biogas constructed in accordance with claim 1:
   wherein said separator includes a centrifuge drum and a conveyor screw rotatable at a differential speed relative to the drum;
   said drive being connected to drive the drum;
   a second drive drivingly connected to drive the screw at a differential speed relative to the drum;
   and a second biogas operated motor connected to said second drive directly.

4. A centrifuge system for treating and separating the solids and liquid phases of sludge of the type which generates biogas constructed in accordance with claim 1:
   including an electric generator connected to be driven by said motor.

5. A centrifuge system for treating and separating the solids and liquid phases of sludge of the type which generates biogas comprising in combination:
   a first centrifugal separator having a sludge inlet and outlets for the liquid phase and solid phase;
   a first drive connected to drive the separator; and
   a digester sludge tower receiving the solids from said separator and generating biogas therefrom,
   a biogas operated first motor receiving biogas from said tower and connected directly to said drive for operation of the separator.

6. A centrifuge system for treating and separating the solids and liquid phases of sludge of the type which generates biogas constructed in accordance with claim 5:
   including a second centrifugal separator having a sludge inlet connected to said sludge tower;
   a second drive connected to drive the second separator;
   a second biogas operated motor connected to said drive for operation of the second separator;
   and second conduit means leading from the tower to said second motor to supply the fuel for operating said second biogas operated motor.

7. A centrifuge system for treating and separating the solids and liquid phases of sludge of the type which generates biogas constructed in accordance with claim 6:
   including a gas collecting chamber in said first and second conduit means receiving biogas from the tower.

8. A centrifuge system for treating and separating the solids and liquid phases of sludge of the type which generates biogas constructed in accordance with claim 6:
   including first and second electrical generators respectively driven by said first and second motors.

9. The method of treating sludge material for separating the material into solids and liquid phases comprising the steps of:
   feeding sludge to a centrifugal separator;
   conveying a solid phase from the separator to a digester and generating a biogas;
   supplying the biogas to an intermediate collection chamber;
   delivering biogas from said collection chamber to drive a gas powered prime mover;
   driving the centrifugal separator with said gas powered prime mover;
   and feeding biogas from said collection chamber to said prime mover at a rate commensurate with the production of biogas.

* * * * *